United States Patent
Aiga

(10) Patent No.: US 12,201,429 B2
(45) Date of Patent: Jan. 21, 2025

(54) CONDUCTIVE FILM, BIOMEDICAL ELECTRODE, AND BIOMEDICAL SENSOR

(71) Applicant: Nitto Denko Corporation, Ibaraki (JP)

(72) Inventor: Takuro Aiga, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 66 days.

(21) Appl. No.: 17/915,386

(22) PCT Filed: Mar. 26, 2021

(86) PCT No.: PCT/JP2021/013087
§ 371 (c)(1),
(2) Date: Sep. 28, 2022

(87) PCT Pub. No.: WO2021/200741
PCT Pub. Date: Oct. 7, 2021

(65) Prior Publication Data
US 2023/0128873 A1  Apr. 27, 2023

(30) Foreign Application Priority Data

Mar. 30, 2020  (JP) ................................ 2020-059653

(51) Int. Cl.
| | |
|---|---|
| H01B 1/20 | (2006.01) |
| A61B 5/268 | (2021.01) |
| C08J 5/18 | (2006.01) |
| C08L 29/04 | (2006.01) |

(52) U.S. Cl.
CPC ............... *A61B 5/268* (2021.01); *C08J 5/18* (2013.01); *C08L 29/04* (2013.01); *H01B 1/20* (2013.01); *C08J 2329/04* (2013.01); *C08J 2465/00* (2013.01); *C08L 2203/16* (2013.01); *C08L 2203/20* (2013.01); *C08L 2312/00* (2013.01)

(58) Field of Classification Search
CPC .... H01B 1/124–128; H01B 1/20; A61B 5/268
See application file for complete search history.

(56) References Cited

U.S. PATENT DOCUMENTS

| | | |
|---|---|---|
| 5,611,339 A | 3/1997 | Okabe et al. |
| 9,084,546 B2 * | 7/2015 | Richardson-Burns ....................... G01N 27/3272 |
| 2004/0135126 A1 * | 7/2004 | Schwark ................ H01B 1/127 252/500 |
| 2006/0057451 A1 * | 3/2006 | Okuzaki ............. H01M 4/8668 429/465 |
| 2014/0020939 A1 * | 1/2014 | Nishio ................... H01B 1/127 428/419 |
| 2020/0286641 A1 * | 9/2020 | Toyoda ................. C08L 101/14 |
| 2021/0005343 A1 * | 1/2021 | Makigawa ............... C08K 3/20 |

FOREIGN PATENT DOCUMENTS

| | | |
|---|---|---|
| CN | 1145037 A | 3/1997 |
| CN | 1742056 A | 3/2006 |
| EP | 3 683 275 A1 | 7/2020 |
| JP | H10-95962 A | 4/1998 |
| JP | 2005-145987 A | 6/2005 |
| JP | 2012-251132 A | 12/2012 |
| JP | 2015-147857 A | 8/2015 |
| TW | 200422338 A | 11/2004 |
| WO | 2016/148249 A1 | 9/2016 |
| WO | 2019/049470 A1 | 3/2019 |

OTHER PUBLICATIONS

Chen et al "Electrically conductive polyaniline-poly(vinyl alcohol) composite films: physical properties and morphological structures", Macromolecules 1991, 24, 1242-1248.*
Li et al "Controlled release of heparin from polypyrrole-poly(vinyl alcohol) assembly by electrical stimulation", Published online Mar. 9, 2005 in Wiley InterScience (www.interscience.wiley.com). DOI: 10.1002/jbm.a.30286.*
International Search Report dated Jun. 22, 2021 for corresponding International Patent Application No. PCT/JP2021/013087, 5 pages.
Written Opinion dated Jun. 22, 2021 for corresponding International Patent Application No. PCT/JP2021/013087, 4 pages.
The Explanation of Circumstances Concerning Accelerated Examination filed on Jun. 24, 2021 for corresponding Japanese Patent Application No. 2021-535957 with English Translation, 5 pages.
Japanese Office Action dated Aug. 31, 2021 for corresponding Japanese Patent Application No. 2021-536237 with English Machine Translation, 7 pages.
The Extended European Search Report issued on Aug. 1, 2023 for European Patent Application No. 21779527.7 (10 pages).
Office Action issued on Aug. 23, 2024, for corresponding Chinese Patent Application No. 202180025305.6, along with an English machine translation (15 pages).

* cited by examiner

*Primary Examiner* — Mark Kopec
(74) *Attorney, Agent, or Firm* — Hauptman Ham, LLP

(57) ABSTRACT

A conductive film includes a cured material having a composition containing a conductive polymer and a binding resin, wherein a water content of the cured material after water absorption is 70% or less.

17 Claims, No Drawings

CONDUCTIVE FILM, BIOMEDICAL ELECTRODE, AND BIOMEDICAL SENSOR

CROSS-REFERENCE TO RELATED APPLICATION

This application is a National Stage of International Application No. PCT/JP2021/013087 filed on Mar. 26, 2021, which designates the United States and was published in Japan, and which is based upon and claims priority to Japanese Patent Application No. 2020-059653 filed on Mar. 30, 2020 in the Japan Patent Office. All of the aforementioned applications are hereby incorporated by reference in their entireties.

TECHNICAL FIELD

The present invention relates to a conductive film, a biomedical electrode, and a biomedical sensor.

BACKGROUND ART

Biomedical sensors for measuring biometric information such as an electrocardiogram, pulse wave, electroencephalogram, myoelectric wave, and the like are used at medical institutions such as hospitals or clinics, nursing care facilities, or homes. The biomedical sensors include biomedical electrodes that contact a living body to obtain biometric information of the living body. In measuring biometric information, a biomedical sensor is applied to the skin of the living body and the biomedical electrode contacts the skin of the living body. The biometric information is measured by acquiring an electrical signal related to the biometric information with the biomedical electrode.

As biomedical electrodes for such biomedical sensors, a biomedical patch electrode is disclosed which is formed using a conductive film configured by, for example, a conductive hydrogel including a specific polymer covalently crosslinked, a conductive material, and a hydrophilic polymer (see, e.g., Patent Document 1).

PRIOR ART DOCUMENTS

Patent Documents

[Patent Document 1] Japanese Patent Application Laid-Open No. 2015-147857

SUMMARY OF INVENTION

Problem to be Solved by the Invention

However, when a biomedical patch electrode containing a conductive polymer is in direct contact with skin, as in the biomedical patch electrode of Patent Document 1, water vapor and sweat (moisture) emitted from the skin are absorbed by the biomedical patch electrode, and the resistance of the biomedical patch electrode may be increased. The amount of sweating of the skin varies depending on a subject, and the skin is subject to excessive evaporation between the biomedical patch electrode and the skin. Therefore, the position where the biomedical patch electrode is applied is in a condition in which humidity is easily changed. Therefore, there is a possibility that the resistance of the biomedical patch electrode will change significantly.

One aspect of the invention is to provide a conductive film capable of suppressing a change in resistance even in a condition in which humidity is easily changed.

Means for Solving Problems

An aspect of a conductive film of the present invention includes a conductive film containing a cured material having a composition containing a conductive polymer and a binding resin, wherein a water content of the cured material after water absorption is 70% or less.

Effects of the Invention

One aspect of the conductive film of the present invention can suppress a change in resistance even in a condition in which humidity is easily changed.

DETAILED DESCRIPTION OF THE INVENTION

Hereinafter, embodiments of the present invention will be described in detail. Unless otherwise noted, in this specification, "to" indicates a numerical range including the numerical values before and after the numerical range as the lower and upper limits.

<Conductive Film>

A conductive film of an embodiment of the present invention will be described. The conductive film of the present embodiment is formed from a cured material of a conductive composition containing a conductive polymer and a binding resin. The conductive film may include other layers in addition to the cured material.

In the conductive film of the present embodiment, a water content of a cured material after water absorption is 70% or less, preferably 65% or less, and more preferably 60% or less.

The water content is calculated by dividing the difference between the mass before drying and the mass after drying, of the conductive film, by the mass before drying of the conductive film as indicated in the following formula (1).

$$\text{(Mass Before Drying} - \text{Mass After Drying)}/\text{Mass Before Drying} \quad (1)$$

The mass before drying refers to the mass of the conductive film before drying and is the mass measured before drying. After drying refers to the state after the conductive film is dried, for example, at 150° C. for 3 minutes. The mass after drying is the mass immediately measured after drying.

The water content of the conductive film both before and after water absorption can also be similarly obtained. Conductive film after water absorption refers to the conductive film being immersed in pure water for at least one hour in a room temperature adjusted to 23° C.±2° C. The mass after absorption is the mass measured immediately after removing the conductive film from the pure water and wiping off the water on the surface of the conductive film.

When a conductive composition including a conductive polymer and a binding resin is cured to form a cured material, a cross-linking agent is generally added to the conductive composition to facilitate crosslinking of the binding resin. In developing the conductive film including the cured material of the conductive composition containing the conductive polymer and the binding resin, the inventor of the present invention has noted that even if a water content is contacted to the conductive film and absorbed, the increase in resistance of the conductive film can be suppressed if the water content of the cured material after water absorption is kept low. In particular, when the binding resin does not contain a cross-linking agent, a hydroxyl group (OH group) is not formed in the cured material, and the increase of the water absorbed by the conductive film tends to be suppressed. The present inventors have found that the increase in resistance of the conductive film can be suppressed or the resistance of the conductive film can be reduced by setting the water content of the conductive film after water absorption to 70% or less.

The conductive film of the present embodiment preferably has a resistance value of the cured material of 120Ω or less, more preferably 112Ω or less, and even more preferably 100Ω or less. If the resistance value of the cured material is 120Ω or less, the conductive film can be more sensitive to the electrical signals obtained from a living body. In addition, the cured material preferably has the resistance value of 120Ω or less before and after water absorption.

In the conductive film of the present embodiment, it is preferable that the upper limit of the water content of the cured material before water absorption is 30%. The water content of the cured material before water absorption is more preferably from 10.5% to 25%, and even more preferably from 11% to 20%. If the water content of the cured material before the water absorption is 30% or less, the conductive film can be maintained in a soft state, so that the conductive film can be easily attached to the surface of the living body.

In the conductive film of the present embodiment, a (W2/W1) of the water content of the conductive film after the water absorption W2 to the water content of the conductive film before the water absorption W1 is preferably 9.0 or less, more preferably 6.5 or less, and even more preferably 6.0 or less. When the W2/W1 of the conductive film is 9.0 or less, a fluctuation amount of the conductive film before and after water absorption is suppressed from becoming too large, and the fluctuation amount of the resistance can be suppressed. The upper limit value is not particularly limited and may be 1.0 or more.

W2/W1 represents the water absorption rate of the conductive film and is calculated by dividing the water content of the conductive film after water absorption W2 by the water content of the conductive film before water absorption W1, as shown in the following formula (2).

Water Absorption Rate of Conductive Film (W2/W1)
=Water Content of Conductive Film After Water Absorption W2/Water Content of Conductive Film Before Water Absorption W1

The conductive film of the present embodiment can be formed using the conductive composition including the conductive polymer and the binding resin. Hereinafter, each component constituting the conductive composition will be described. The conductive polymer and the binding resin, which are essential components of conductive compositions, are described.

For example, a polythiophene-based conductive polymer, a polyaniline-based conductive polymer, a polypyrrole-based conductive polymer, a polyacetylene-based conductive polymer, a polyphenylene-based conductive polymer, and derivatives thereof, and a composite thereof may be used as the conductive polymer. These may be used alone or in combination with two or more kinds.

Examples of polythiophene-based conductive polymers include poly(thiophene), poly(3-methylthiophene), poly(3-ethylthiophene), poly(3-propylthiophene), poly(3-butylthiophene), poly(3-hexylthiophene), poly(3-heptylthiophene), poly(3-octylthiophene), poly(3-decylthiophene), poly(3-dodecylthiophene), poly(3-octadecylthiophene), poly(3-bromothiophene), poly(3-chlorothiophene), poly(3-iodothiophene), poly(3-cyanothiophene), poly(3-cyanothiophene), poly(3-phenylthiophene), poly(3,4-dimethylthiophene), poly(3,4-dibutylthiophene), poly(3-hydroxythiophene), poly(3-methoxythiophene), poly(3-methoxythiophene), poly(3-ethoxythiophene), poly(3-butoxythiophene), poly(3-hexyloxythiophene), poly(3-octyloxythiophene), poly(3-decyloxythiophene), poly(3-dodecyloxythiophene), poly(3-octadecyloxythiophene), poly(3,4-dihydroxythiophene), poly(3,4-dimethoxythiophene), poly(3,4-diethoxythiophene), poly(3,4-dipropoxythiophene), poly(3,4-dibutoxythiophene), poly(3,4-dibutoxythiophene), poly(3,4-dihexyloxythiophene), poly(3,4-diheptyloxythiophene), poly(3,4-dioctyloxythiophene), poly(3,4-didecyloxythiophene), poly(3,4-didodecyloxythiophene), poly(3,4-ethylenedioxythiophene) (also referred to as PEDOT), poly(3,4-propylene dioxythiophene), poly(3,4-butenedioxythiophene), poly(3-methyl-4-methoxythiophene), poly(3-methyl-4-ethoxythiophene), poly(3-carboxythiophene), poly(3-methyl carboxythiophene), poly(3-methyl carboxyethylthiophene), and poly(3-methyl carboxybutylthiophene), and the like.

Examples of polyanionic conductive polymers include polyaniline; polymers having sulfonic acid groups such as polystyrene sulfonic acid (also referred to as PSS), polyvinyl sulfonic acid, polyallyl sulfonic acid, polyacryl sulfonic acid, poly(2-acrylamide methyl propane sulfonic acid), polyisoprene sulfonic acid, polysulfoethyl methacrylate, poly(4-sulfobutyl methacrylate), polymethacryloxybenzene sulfonic acid, and the like; polymers having polyacrylic acid groups such as polyvinyl carboxylic acid, polystyrene carboxylic acid, polyallyl carboxylic acid, polyacrylic carboxylic acid, polymethacrylic carboxylic acid, polymethacrylic acid, poly(2-acrylamide-2-methylpropane carboxylic acid), polyisoprene carboxylic acid, and the like. These may be used as a homopolymer obtained by polymerizing one kind alone, or may be used as a copolymer of two or more kinds. Among these polyanions, a polymer having a sulfonic acid group is preferably used, and polystyrene sulfonic acid is more preferably used, in terms of increasing conductivity.

Examples of polypyrrole-based conductive polymers include polypyrrole, poly(N-methylpyrrol), poly(3-methylpyrrol), poly(3-ethylpyrrole), poly(3-n-propylpyrrol), poly(3-butylpyrrol), poly(3-octylpyrrole), poly(3-decylpyrrol), poly(3-dodecylpyrrole), poly(3,4-dimethylpyrrol), poly(3,4-dibutylpyrrol), poly(3-carboxypyrrol), poly(3-methyl-4-carboxyethylpyrrol), poly(3-methyl-4-carboxybutylpyrrol), poly(3-hydroxypyrol), poly(3-methoxypyrrol), poly(3-ethoxypyrrol), poly(3-butoxypyrrol), poly(3-butoxypyrrol), poly(3-hexyloxypyrrole), poly(3-methyl-4-hexyloxypyrrole), and the like.

The polyacetylene can be appropriately synthesized, and examples of the polyacetylene include a polyacetylene having a polar group such as a polyphenylacetylene monoester having an ester at the para position of phenylacetylene and a polyphenylacetylene monoamide having an amide at the para position of phenylacetylene.

Examples of polyphenylene-based conductive polymers include polyphenylene vinylene and the like.

Examples of these composites include polyaniline doped with polythiophene as a dopant. As a composite of polythiophene and polyaniline, a PEDOT/PSS doped with PSS in PEDOT or the like can be used.

As a conductive polymer, among the above, a composite of polythiophene doped with polyaniline as a dopant is preferably used. Among composites of polythiophene and polyaniline, PEDOT/PSS doped with PSS in PEDOT is more preferably used because of its lower contact impedance with living body and its high electrical conductivity.

The content of the conductive polymer is preferably 0.20 to 20 parts by mass, more preferably 2.5 to 15 parts by mass, and even more preferably 3.0 to 12 parts by mass with respect to 100 parts by mass of the conductive composition. If the content is 0.20 to 20 parts by mass with respect to the conductive composition, the conductive composition can have excellent conductivity, toughness, and flexibility.

The conductive polymer may be used as an aqueous solution dissolved in a solvent. In this case, an organic solvent or a water-based solvent may be used as the solvent. Examples of the organic solvents include ketones such as acetone, methyl ethyl ketone (MEK), and the like; esters such as ethyl acetate and the like; ethers such as propylene glycol monomethyl ether and the like; and amides such as N,N-dimethylformamide and the like. Examples of the aqueous solvents include water; alcohols such as methanol, ethanol, propanol, isopropanol, and the like. Among these, the aqueous solvent is preferably used.

The binding resin may be a water-soluble polymer or a water-insoluble polymer. The binding resin preferably employs water soluble polymers in terms of compatibility with other components included in the conductive composition. It should be noted that the water-soluble polymer is not completely soluble in water and may include a polymer having hydrophilicity (hydrophilic polymer).

As the water-soluble polymer, a hydroxyl-containing polymer or the like may be used. As the hydroxyl group-containing polymer, a sugar such as agarose, a polyvinyl alcohol (PVA), a modified polyvinyl alcohol, a copolymer of acrylic acid and sodium acrylate, or the like can be used. These may be used alone or in combination with two or more kinds. Among these, polyvinyl alcohol or modified polyvinyl alcohol is preferably used, and the modified polyvinyl alcohol is more preferably used.

Examples of the modified polyvinyl alcohols include acetoacetyl-containing polyvinyl alcohol, diacetone acrylamide-modified polyvinyl alcohol, and the like. As the diacetone acrylamide modified polyvinyl alcohol, for example, a diacetone acrylamide modified polyvinyl alcohol resin (DA modified PVA resin) described in Japanese Patent Application Laid-Open No. 2016-166436 may be used.

The content of binding resin is preferably 5 to 140 parts by mass relative to 100 parts by mass of the conductive composition, more preferably 10 to 100 parts by mass, and even more preferably 20 to 70 parts by mass. If the content is within the above preferred range for the conductive composition, the cured material obtained using the conductive composition can have excellent conductivity, toughness, and flexibility.

The binding resin may be used as an aqueous solution dissolved in the solvent. The solvent may be the same solvent as in the case of the conductive polymer described above.

The conductive composition further preferably includes either a cross-linking agent, or a plasticizer, or both. The conductive composition preferably does not contain the cross-linking agent. The cross-linking agent and the plasticizer impart toughness and flexibility to the cured material obtained using the conductive composition.

Toughness is a property that achieves both excellent strength and elongation. Toughness does not include properties that are significantly superior in one of strength and elongation but significantly lower in the other. Toughness includes properties that have an excellent balance of both strength and elongation.

Flexibility is a property that prevents damage such as fracture from occurring in the bent portion after the cured material containing the conductive composition is bent.

The cross-linking agent functions to cross-link the binding resin. The inclusion of a cross-linking agent in the binding resin can improve the toughness of the cured material obtained by using the conductive composition. The cross-linking agent should have reactivity with hydroxyl groups. If the cross-linking agent is reactive with hydroxyl groups, then when the binding resin is a hydroxyl group-containing polymer, the cross-linking agent can react with the hydroxyl groups of the hydroxyl group-containing polymer.

Examples of the cross-linking agents include zirconium compounds such as zirconium salts; titanium compounds such as titanium salts; boron compounds such as boric acid; isocyanate compounds such as block isocyanate; aldehyde compounds such as sodium glyoxylate, formaldehyde, acetaldehyde, glyoxal, glutaraldehyde; alkoxyl group-containing compounds; methylol group-containing compounds; and the like. These may be used alone or in combination with two or more kinds. Among them, when the binding resin is a porvinyl alcohol, sodium glyoxylate is preferable because the binding resin tends to react with the porvinyl alcohol to form a crosslinked structure, and the properties of the cured material obtained using the conductive composition is easily maintained.

The content of the cross-linking agent is preferably 0.01 to 5.6 parts by mass, more preferably 1.0 to 5.0 parts by mass, and even more preferably 1.4 to 3.0 parts by mass with respect to 100 parts by mass of the conductive composition. If the content is within the above-described preferred range, the cures material obtained using the conductive composition can have excellent toughness and flexibility.

The cross-linking agent may be used as an aqueous solution dissolved in the solvent. The solvent may be the same solvent as in the case of the conductive polymer described above.

The plasticizer has the function of improving the conductivity of the cured material obtained using the conductive composition, as well as improving tensile elongation and flexibility. Examples of the plasticizers include polyol compounds such as glycerin, ethylene glycol, propylene glycol, sorbitol, and the like; aprotic compounds such as N-methylpyrrolidone (NMP), dimethylformaldehyde (DMF), N—N'-dimethylacetamide (DMAc), dimethyl sulfoxide (DMSO), and the like. These may be used alone or in combination with two or more kinds. Among these, glycerin is preferably used from the viewpoint of compatibility with other components.

The content of the plasticizer with respect to 100 parts by mass of the conductive composition is preferably 0.2 to 150 parts by mass, more preferably 1.0 to 90 parts by mass, and even more preferably 10 to 70 parts by mass. If the content is within the above-described preferred range, the cured material obtained using the conductive composition can have excellent toughness and flexibility.

The conductive composition includes either a cross-linking agent, a plasticizer, or the both so that the cured material obtained using the conductive composition can have improved toughness and flexibility.

When the conductive composition contains the cross-linking agent but does not contain the plasticizer, the cured material obtained using the conductive composition can have both improved toughness, for example, tensile strength and tensile elongation, and improved flexibility.

If the conductive composition contains the plasticizer but does not contain the cross-linking agent, the cured material obtained using the conductive composition as a whole can have improved tensile elongation of the resulting cured material, and hence the cured material obtained using the conductive composition can have improved toughness. It is also possible to improve the flexibility of the cured material obtained using the conductive composition.

Both the cross-linking agent and the plasticizer are preferably included in the conductive composition. Both the cross-linking agent and the plasticizer are included in the conductive composition. Therefore, the cured material obtained using the conductive composition can have even greater toughness.

In addition to the above components, the conductive composition may optionally contain any of a variety of known additives, such as surfactants, softeners, stabilizers, leveling agents, antioxidants, antihydrolysis agents, swelling agents, thickeners, colorants, fillers, and the like, as needed. Examples of the surfactants include a silicone-based surfactant and the like.

The conductive composition is prepared by mixing each of the above components in the above ratio.

The conductive composition may optionally include the solvent in any proportion. This allows to prepare an aqueous solution of the conductive composition (aqueous conductive composition solution).

The solvent may be the same solvent as used in the conductive polymer described above.

An example of a method of manufacturing the conductive film will be described.

The conductive composition including the conductive polymer and the binding resin is prepared by mixing the conductive polymer and the binding resin in the ratio described above. The conductive composition may further include either the cross-linking agent, the plasticizer, or the both at the ratio described above. When preparing the conductive composition, the conductive polymer, the binding resin, and the cross-linking agent may be used as the aqueous solution dissolved in the solvent.

The conductive composition may optionally contain the solvent including the conductive polymer, the binding resin, and the cross-linking agent, as well as the solvent in any suitable proportion, using the aqueous solution of the conductive composition. A similar solvent to the above-described solvent may be used as the solvent.

After the conductive composition is applied to a surface of a release substrate, the conductive composition is heated to allow the cross-linking reaction of the binding resin contained in the conductive composition to proceed and cure the binding resin to provide a cured material of the conductive composition. The surface of the resulting cured material is punched out (pressed) or the like using a press or the like, as needed, to form one or more through-holes on the surface of the cured material and to form the shape of the cured material into a predetermined shape. This results in obtaining a conductive electrode which is a formed into a film having one or more through holes on its surface and having a predetermined shape. Alternatively, the cured material may be formed by a laser processing machine instead of the press machine. The resulting cured material may also form only one or more through-holes on its surface, or it may form only an external shape in a predetermined shape. Furthermore, if the cured material can be used as a conductive film, the cured material may be used as a conductive film without shaping or the like.

Each of the components of the conductive polymer, binding resin, cross-linking agent, and plasticizer contained in the conductive film has an amount equivalent to the amount added when manufacturing the conductive composition.

As the release substrate, a separator, a core material, or the like may be used. The separator may be a resin film such as a polyethylene terephthalate (PET) film, a polyethylene terephthalate (PE) film, a polypropylene (PP) film, a polyamide (PA) film, a polyimide (PI) film, or a fluoropolymer film.

As the core material, a resin film, such as a PET film or a PI film; a ceramic sheet; a metal film such as aluminum foil; a resin substrate reinforced with glass fibers or plastic non-woven fibers; a silicone substrate or a glass substrate may be used.

As a method of applying the conductive composition onto a release substrate, a method by roll coating, screen coating, gravure coating, spin coating, reverse coating, bar coating, blade coating, air knife coating, dipping, dispensing, or the like, a method by hanging a small amount of the conductive composition over the substrate and stretching it with a doctor blade, or the like can be used. By these coating methods, the conductive composition is uniformly coated onto the release substrate.

The conductive composition can be heated by known dryers such as drying ovens, vacuum ovens, air circulation ovens, hot air dryers, far infrared dryers, microwave vacuum dryers, high frequency dryers, and the like.

The heating conditions may be such that the cross-linking agent contained in the conductive composition can react.

The heating temperature of the conductive composition is such that the curing of the binding resin contained in the conductive composition can proceed. The heating temperature is preferably 100° C. to 200° C. If the conductive composition contains the cross-linking agent, the reaction of the cross-linking agent can be facilitated and the curing of the binding resin can be facilitated if the heating temperature is in the range of 100° C. to 200° C.

The heating time of the conductive composition is preferably from 0.5 minutes to 300 minutes, and more preferably from 5 minutes to 120 minutes. The binding resin can be fully cured if the heating time is in the range of 0.5 to 300 minutes.

As described above, the conductive film of the present embodiment includes the cured material of the conductive composition and has the water content after water absorption of 70%. When the conductive film is immersed in water to absorb water into the cured material, in addition to the immersion of water into the gaps inside the cured material and the immersion of water into the cross-linked structure of the cured material, there are other factors that cause water absorption, such as the aldehyde reaction of the acetoacetyl group, which becomes the cross-linking point with the binder resin contained in the conductive composition when the cross-linking agent is added to the conductive composition, and the bonding to the hydroxyl group (OH group) generated as the cross-linking reaction progresses. For example, when polyvinyl alcohol is used as the binding resin, the OH group formed by the aldehyde reaction with the acetoacetyl group, which is the cross-linking point with the polyvinyl alcohol as indicated in the following reaction formula, becomes the water binding moiety.

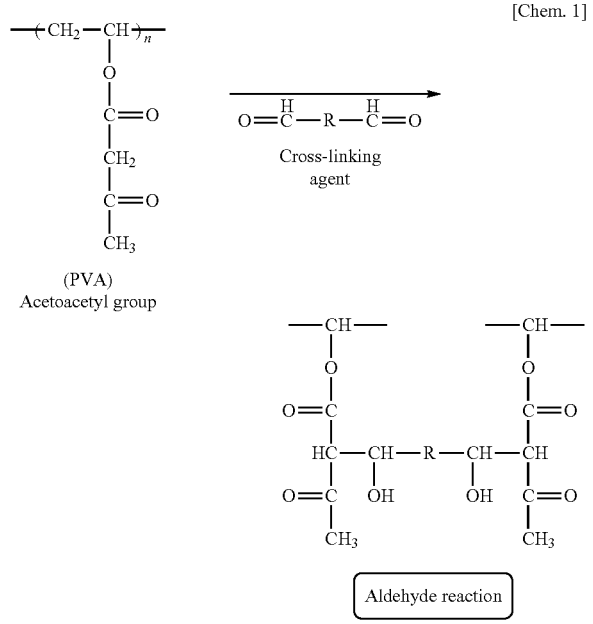

[Chem. 1]

The water content of the conductive film increases to a certain extent after the water absorption, because the amount of water supplied due to the immersion of water into the gap inside the cured material and the immersion of water into the crosslinked structure of the cured material does not appreciably change. When the water content of the conductive film after the water absorption is 70% or less, the water absorption amount of the cured product is mostly due to the immersion of water into the gap inside the cured product and the immersion of water into the crosslinked structure of the cured product. Therefore, the conductive film of the present embodiment can suppress a change in resistance even in a condition in which humidity is easily changed.

The lower the resistance of the cured material produced using the conductive composition and the higher the conductivity, the lower the contact impedance of the conductive film with the living body and the higher the sensitivity of detecting the electrical signal obtained from the living body, thereby increasing the accuracy of measuring the biomedical electrode when the conductive film is used as the biomedical electrode. When the contact impedance is lower, the biometric information can be stably and accurately measured. When the contact impedance is 500Ω or less, the electrocardiogram can be stably measured as the biometric information.

In the conductive film of the present embodiment, the resistance value of the cured material of the conductive composition is 120Ω or less. This allows the conductive film to detect the electrical signal obtained from the living body with higher sensitivity when the conductive film is used for the biomedical electrode. Therefore, even when the conductive film is provided in a condition in which humidity is easily changed, such as the surface of the living body, the measurement accuracy of the biometric information can be stably increased.

Further, the conductive film of the present embodiment can have a water content of 30% or less before water absorption of the cured material of the conductive composition. As a result, the conductive film can be stably flexible even when the conductive film is provided in a condition in which humidity is easily changed, so that the conductive film can be maintained attached to the surface of the living body.

The conductive film of the present embodiment can have a water absorption rate of the cured material of the conductive composition (W2/W1) of 9.0 or less. By suppressing the increase in water content before and after the water absorption of the cured material of the conductive composition, the conductive film of the present embodiment can more stably suppress changes in resistance even when the conductive film is provided in a condition in which humidity is easily changed.

In addition, the conductive film of the present embodiment may be a cured material containing 0.01 to 5.6 parts by mass of the cross-linking agent in the conductive composition. If the amount of the cross-linking agent contained in the conductive composition is suppressed, the amount of the OH group produced in the cured material of the conductive composition by the crosslinking reaction between the binding resin and the cross-linking agent can be reduced, and the increase in the amount of water absorption can be suppressed. For example, when the binder layer is a polyvinyl alcohol, as noted above, the acetoacetyl group of the polyvinyl alcohol forms a cross-linking structure by an aldehyde reaction with the cross-linking agent to form a hydrophilic OH group during the cross-linking of the polyvinyl alcohol. The progress of this cross-linking reaction leads to the increase in the percentage of OH groups and the increase in water absorption. The conductive film of the present embodiment can suppress the formation of the OH group in the cured material and suppress the increase in the amount of water absorbed when the cured material absorbs water. Therefore, a variation before and after water absorption can be suppressed. Therefore, even when the conductive film of the present embodiment is provided in a condition in which humidity is easily changed, the change in resistance can be further stably suppressed.

The conductive film of the present embodiment can use a cured material which is cured without including the cross-linking agent in the conductive composition. If the conductive composition does not contain the cross-linking agent, the OH group is not formed in the cured material of the conductive composition. Therefore, it is possible to prevent an increase in the amount of water absorbed due to the bond of water to the OH group formed in the cured material, which is one of the factors of water absorption. Therefore, if the conductive film of the present embodiment does not contain the cross-linking agent, the variation before and after water absorption can be further suppressed. Therefore, even when the conductive film is provided in a condition in which humidity is easily changed, the change in resistance can be more stably suppressed.

In addition, the conductive film of the present embodiment can increase the conductivity by using the cured material in which the conductive composition not having the cross-linking agent is cured. For example, when PEDOT/PSS is used as the conductive polymer and sodium glyoxylate is used as the cross-linking agent, it is considered that the Na ions (Na+) contained in the cross-linking agent replace the hydrogen ions (H+) and PEDOT of $SO_3H$ that constitute the PSS of the PEDOT/PSS as indicated in the following reaction formula to inhibit the transfer of electrons within the PEDOT/PSS. This suggests that the bipolaron (dication) produced by PSS extracting electrons from the PEDOT inhibits hopping conduction between molecules. The conductive film of the present embodiment can further enhance the conductivity by using the cured material in which the conductive composition not having the cross-linking agent is cured, thereby preventing the movement of electrons from being inhibited.

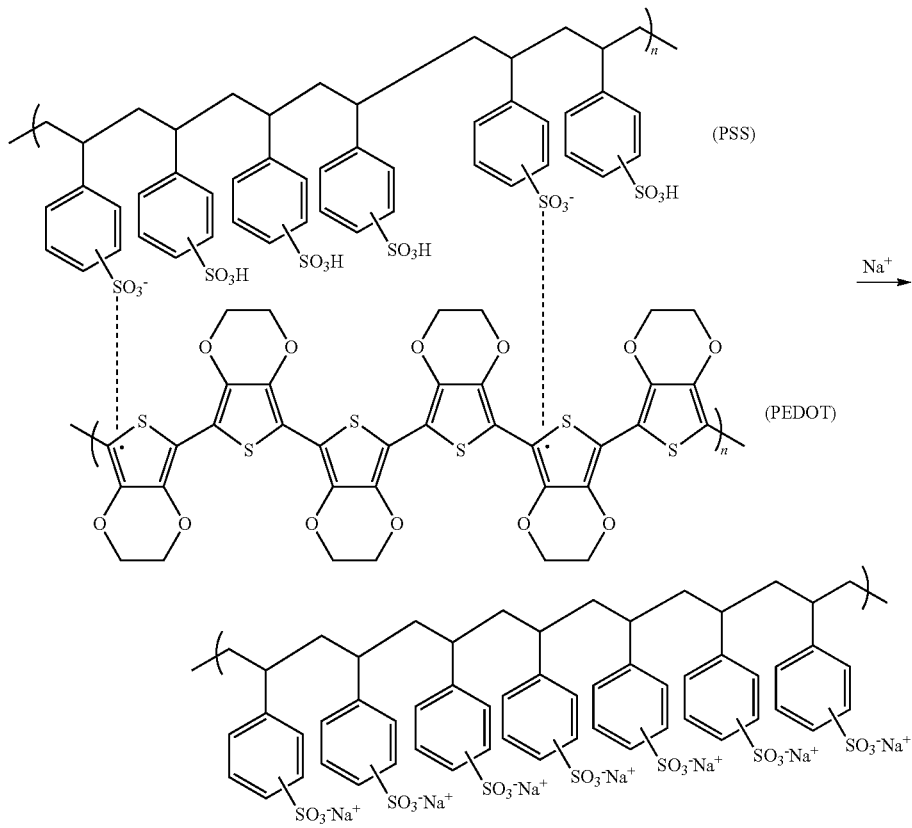

[Chem. 2]

The conductive composition of the present embodiment has the properties described above. Therefore, by including the cured material of the conductive composition as a material for electrodes for biological sensors (biomedical electrode), the conductive composition can be effectively used as a biomedical electrode. The biomedical electrode can be of any shape, such as a sheet or the like.

The biomedical electrode formed using the conductive composition of the present embodiment has high conductivity and is capable of reducing irritation to the skin. Therefore, the biomedical electrode can be suitably used as a biomedical electrode of a patch-type biomedical sensor applied to a biomedical sensor, particularly to the skin of a living body, which requires high conductivity and safety to the skin.

EXAMPLES

Hereinafter, although Examples and Comparative Examples are indicated and described in further detail, embodiments are not limited by these Examples and Comparative Examples.

Example 1

[Preparation of Electrode Sheet]
(Preparation of Conductive Composition)

0.38 parts by mass of PEDOT/PSS pellet (Orgacon DRY, manufactured by AGFA Materials Japan, Ltd.) as the conductive polymer, 10.0 parts by mass of the aqueous solution containing modified polyvinyl alcohol as the binding resin (denatured polyvinyl alcohol concentration: 10%, "GOHSENX Z-410," manufactured by Nippon Gohsei Limited) and 2.0 parts by mass of glycerin (manufactured by Wako Pure Chemical Co., Ltd.) as the plasticizer were added to an ultrasonic bath. The aqueous solution containing these components was then mixed in the ultrasonic bath for 30 minutes to prepare a uniform aqueous conductive composition solution.

Approximately 20% of the pellet of PEDOT/PSS is dissolved in water, so that the content of PEDOT/PSS in an aqueous solution of the conductive composition is 0.308 parts by mass. The concentration of the modified polyvinyl alcohol in the aqueous solution containing the modified polyvinyl alcohol is 10%. Therefore, the content of the modified polyvinyl alcohol in the aqueous conductive composition solution is 1.00 parts by mass. The remainder is the solvent in the aqueous conductive composition solution.

The contents of the conductive polymer, binding resin, and plasticizer with respect to 100 parts by mass of the conductive composition were 9.3 parts by mass, 30.2 parts by mass, and 60.5 parts by mass, respectively.

(Preparation of Conductive Film)

The prepared aqueous conductive composition solution was coated onto a polyethylene terephthalate (PET) film using an applicator. Thereafter, the PET film coated with the aqueous conductive composition solution was transferred to a drying oven (SPHH-201, manufactured by ESPEC) to heat and dry the aqueous conductive composition solution at 120° C. for 10 minutes to prepare a cured material of the conductive composition. The cured material was pressed to form a sheet, and a conductive film was prepared as a formed body with a thickness of 25 μm. The conductive film was divided into three conductive films.

[Evaluation of Conductive Film]

The water content and resistance before water absorption, the water content and resistance after water absorption, and the water absorption rate, which is the amount of change in water content before and after water absorption, of the resulting conductive film were measured and evaluated. In each measurement, three conductive films were subjected to be measure under the same conditions, and the average value was calculated and evaluated.

(Evaluation of Water Content of Conductive Film Before Absorption)

After weighing the resulting conductive film before drying, the conductive film was heated to dry in a drying oven (SPHH-201, manufactured by ESPEC) at 150° C. for 3 minutes to determine the mass after drying. The water content of the conductive film before water absorption was calculated based on the following formula (11).

$$W1 = (\text{Mass of Conductive Film After Drying} - \text{Mass of Conductive Film Before Drying})/\text{Mass of Conductive Film Before Drying} \times 100 (\%) \quad (11)$$

(Evaluation of Resistance Value Before Absorption of Conductive Film)

The resistance of the conductive film before water absorption was measured by connecting a lead wire of a resistance measuring device (3803 DIGITAL HiTESTER, manufactured by HIOKI E.E. CORPORATION) to a metal plate and pressing the conductive film against the surface of the metal plate.

(Evaluation of Water Content of Conductive Film after Water Absorption)

The resulting conductive film was immersed in pure water in a water bath for 60 minutes, then the conductive film was removed from the water bath, and water on the surface of the conductive film was wiped off, and the mass was immediately measured. The conductive film was then heated to dry at 150° C. for 3 minutes in a drying oven (SPHH-201, manufactured by ESPEC) and the mass after drying was measured. The water content of the conductive film after water absorption was calculated based on the following formula (12).

$$W2 = (\text{Mass of Water-Absorbed-Conductive Film After Drying} - \text{Mass of Water-Absorbed-Conductive Film Before Drying})/\text{Mass of Water-Absorbed-Conductive Film Before Drying} \times 100 (\%) \quad (12)$$

(Evaluation of Resistance Value of Conductive Film after Water Absorption)

The resistance of the conductive film after water absorption was measured as described above (evaluation of resistance value of the conductive film before water absorption).

(Evaluation of Water Absorption Rate of Conductive Film)

The water absorption rate of the conductive film was calculated based on the following formula (2).

$$\text{Water Absorption Rate of Conductive Film} = \text{Water Content of Conductive Film After Water Absorption}/\text{Water Content of Conductive Film Before Water Absorption} \quad (2)$$

Example 2

Example 2 was performed in the same manner as in Example 1, except that 0.5 parts by mass of a solution containing sodium glyoxylate ("SAFELINK (registered trademark) SPM-01 (10%)", manufactured by Mitsubishi Chemical Corporation) as a cross-linking agent was added to the aqueous conductive composition solution. The concentration of sodium glyoxylate in the aqueous solution containing sodium glyoxylate is about 10%. Therefore, the content of sodium glyoxylate in the aqueous conductive composition solution is 0.05 parts by mass.

The content of each component (conductive polymer, binding resin, cross-linking agent, and plasticizer) in the conductive composition prepared in this example was 9.2 parts by mass, 29.8 parts by mass, 1.5 parts by mass, and 59.6 parts by mass, respectively, with respect to 100.00 parts by mass of the conductive composition.

Example 3

Example 3 was performed in the same manner as in Example 1, except that 1.0 parts by mass of a solution containing sodium glyoxylate ("SAFELINK (registered trademark) SPM-01 (10%)", manufactured by Mitsubishi Chemical Corporation) as a cross-linking agent was added to the aqueous conductive composition solution, and also except that the content of sodium glyoxylate in the aqueous conductive composition solution was adjusted to 0.10 parts by mass.

The content of each component (conductive polymer, binding resin, cross-linking agent, and plasticizer) in the conductive composition prepared in this example was 9.0 parts by mass, 29.3 parts by mass, 2.9 parts by mass, and 58.7 parts by mass, respectively, with respect to 100.00 parts by mass of the conductive composition.

Comparative Example 1

Comparative Example 1 was performed in the same manner as in Example 1, except that 2.0 parts by mass of a solution containing sodium glyoxylate ("SAFELINK (registered trademark) SPM-01 (10%)", manufactured by Mitsubishi Chemical Corporation) as a cross-linking agent was added to the aqueous conductive composition solution, and also except that the content of sodium glyoxylate in the aqueous conductive composition solution was adjusted to 0.20 parts by mass.

The content of each component (conductive polymer, binding resin, cross-linking agent, and plasticizer) in the conductive composition prepared in this example was 8.8 parts by mass, 28.5 parts by mass, 5.7 parts by mass, and 57.0 parts by mass, respectively, with respect to 100.00 parts by mass of the conductive composition.

Comparative Example 2

Comparative Example 2 was performed in the same manner as in Example 1, except that 5.0 parts by mass of a solution containing sodium glyoxylate ("SAFELINK (registered trademark) SPM-01 (10%)", manufactured by Mitsubishi Chemical Corporation) as a cross-linking agent was added to the aqueous conductive composition solution, and also except that the content of sodium glyoxylate in the aqueous conductive composition solution was adjusted to 0.50 parts by mass.

The content of each component (conductive polymer, binding resin, cross-linking agent, and plasticizer) in the conductive composition prepared in this example was 8.1 parts by mass, 26.3 parts by mass, 13.1 parts by mass, and 52.5 parts by mass, respectively, with respect to 100.00 parts by mass of the conductive composition.

Comparative Example 3

Comparative Example 3 was performed in the same manner as in Example 1, except that 10.0 parts by mass of a solution containing sodium glyoxylate ("SAFELINK (registered trademark) SPM-01 (10%)", manufactured by Mitsubishi Chemical Corporation) as a cross-linking agent was added to the aqueous conductive composition solution, and also except that the content of sodium glyoxylate in the aqueous conductive composition solution was adjusted to 1.0 parts by mass.

The content of each component (conductive polymer, binding resin, cross-linking agent, and plasticizer) in the conductive composition prepared in this example was 7.1 parts by mass, 23.2 parts by mass, 23.2 parts by mass, and 46.4 parts by mass, respectively, with respect to 100.00 parts by mass of the conductive composition.

Table 1 indicates the measurement results of the water content W1 and its resistance value before the water absorption, the water content W2 and its resistance value after the water absorption, and the water absorption rate of the obtained conductive film in each Example and Comparative Example. It should be noted that the brackets for each component in Table 1 indicate "mass" when the total mass of the component obtained by removing the solvent from the aqueous conductive composition solution is set to 100 parts by mass.

electrical signal obtained from the subject with a high sensitivity. Thus, the biomedical sensor can be effectively used to stably measure an electrocardiogram for a long period of time (for example, 24 hours) in close contact with the subject's skin.

Although the embodiments have been described as above, the embodiments are presented by way of example and the invention is not limited by the embodiments. The embodiments may be implemented in various other forms, and various combinations, omissions, substitutions, modifications, or the like, may be made without departing from the spirit of the invention. These embodiments and modifications thereof are included in the scope and gist of the invention and fall within the scope of the claimed invention and equivalents thereof.

The present application is based on and claims priority of Patent Application No. 2020-059653, filed Mar. 30, 2020 with the Japan Patent Office, the entire contents of Japanese Patent Application No. 2020-059653 are hereby incorporated by reference.

The invention claimed is:
1. A conductive film comprising:
a cured material having a composition containing a conductive polymer and a binding resin, wherein
a first water content of the cured material in an immersed state is 70% or less,
the immersed state of the cured material is a state of the conductive film immersed in pure water for at least one hour at 23° C.±2° C.,
a ratio of the first water content of the cured material in the immersed state to a second water content of the cured material in a dried state is 9.0 or less, and
the dried state of the cured material is a state of the conductive film dried at 150° C. for 3 minutes.

2. The conductive film according to claim 1, wherein a resistance value of the cured material is 120Ω or less.

3. The conductive film according to claim 1, wherein the second water content of the cured material in the dried state is 30% or less.

4. The conductive film according to claim 1, wherein the composition contains 0.01 parts by mass or more and 5.6 parts by mass or less of a cross-linking agent.

5. The conductive film according to claim 1, wherein the composition does not contain a cross-linking agent.

TABLE 1

| | Aqueous conductive composition solution Composition (parts by mass) | | | | | | Conductive film | | | | |
|---|---|---|---|---|---|---|---|---|---|---|---|
| | | | | | | | Water content before | Resistance value before | Water content after | Resistance value after | Rate |
| | Conductive polymer | Binding resin | Cross-linking agent | Plasticizer | Total | Remainder | water absorption W1[%] | water absorption [Ω] | water absorption W2[%] | water absorption [Ω] | of water absorption |
| Example 1 | 0.308 (9.3) | 1.00 (30.2) | 0.00 (0.00) | 2.00 (60.5) | 3.308 (100.00) | 96.692 (—) | 11 | 51 | 65 | 28 | 5.91 |
| Example 2 | 0.308 (9.2) | 1.00 (29.8) | 0.05 (1.5) | 2.00 (59.6) | 3.358 (100.00) | 96.642 (—) | 11 | 57 | 69 | 72 | 6.27 |
| Example 3 | 0.308 (9.0) | 1.00 (29.3) | 0.10 (2.9) | 2.00 (58.7) | 3.408 (100.00) | 96.592 (—) | 11 | 111 | 65 | 80 | 5.91 |
| Comparative Example 1 | 0.308 (8.8) | 1.00 (28.5) | 0.20 (5.7) | 2.00 (57.0) | 3.508 (100.00) | 96.492 (—) | 10 | 145 | 95 | 780 | 9.50 |
| Comparative Example 2 | 0.308 (8.1) | 1.00 (26.3) | 0.50 (13.1) | 2.00 (52.5) | 3.808 (100.00) | 96.192 (—) | 9.0 | 175 | 96 | 1580 | 10.67 |
| Comparative Example 3 | 0.308 (7.1) | 1.00 (23.2) | 1.00 (23.2) | 2.00 (46.4) | 4.308 (100.00) | 95.692 (—) | 5.3 | 292 | 96 | 3580 | 18.11 |

As indicated in Table 1, in Examples 1 to 3, the water content of the conductive film after the water absorption W2 was 69% or less. On the other hand, in Comparative Examples 1 to 3, the water content of the conductive film after the water absorption W2 was 95% or more.

Accordingly, unlike the conductive films of Comparative Examples 1 to 3, the conductive films of Examples 1 to 3 have water content of W2 of 69% or less after the conductive film is absorbed in water, and it can be said that the increase in resistance is suppressed. Accordingly, when the conductive film of the present embodiment is used as a biomedical electrode of a biomedical sensor, it is possible to prevent a decrease in the conductivity. Therefore, it is possible to maintain the contact impedance of the conductive film with a subject at a low level, and it is possible to stably detect an 6. A biomedical electrode comprising the conductive film of claim 1.

7. A biomedical sensor comprising the biomedical electrode of claim 6.

8. A conductive film comprising:
a cured material comprising a composition containing a conductive polymer and a binding resin, wherein
a first water content of the cured material corresponds to a first state of the conductive film first dried at 150° C. for 3 minutes,
a second water content of the cured material corresponds to a second state of the conductive film immersed in pure water for at least one hour at 23° C.±2° C. and second dried at 150° C. for 3 minutes, and
a ratio of the second water content to the first water content is 9.0 or less.

9. The conductive film of claim 8, wherein the second water content is 70% or less.

10. The conductive film of claim 9, wherein the first water content is 30% or less.

11. The conductive film of claim 8, wherein the first water content is 30% or less.

12. The conductive film of claim 8, wherein a resistance value of the cured material is 120Ω or less.

13. The conductive film of claim 8, wherein
the cured material has a first resistance value corresponding to the first state and a second resistance value corresponding to the second state, and
the second resistance value is within ±45% of the first resistance value.

14. The conductive film according to claim 8, wherein the composition contains 0.01 parts by mass or more and 5.6 parts by mass or less of a cross-linking agent.

15. The conductive film according to claim 8, wherein the composition does not contain a cross-linking agent.

16. A biomedical electrode comprising the conductive film of claim 8.

17. A biomedical sensor comprising the biomedical electrode of claim 16.

* * * * *